Figure 1:
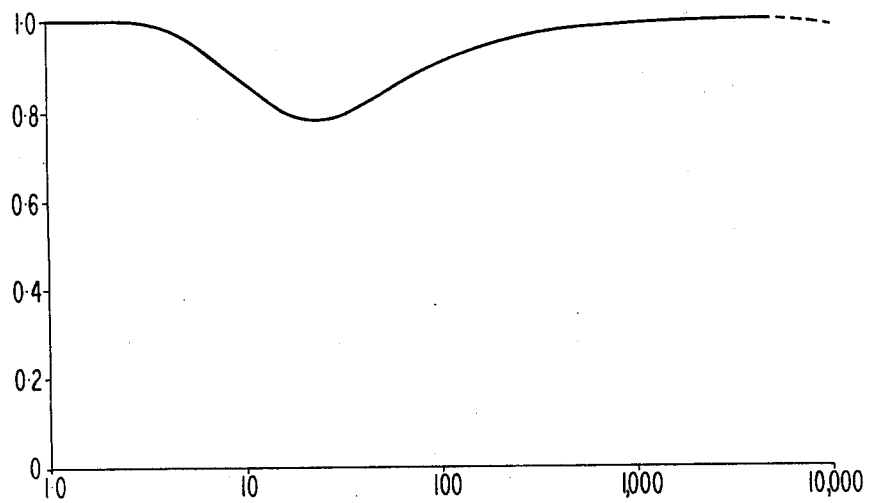

United States Patent [19]  
Maslen et al.

[11] 4,306,026  
[45] Dec. 15, 1981

[54] PROCESS FOR CULTURING CELLS

[75] Inventors: Frank P. Maslen; John C. Ousby; Peter J. Senior, all of Stockton-on-Tees, England

[73] Assignee: Imperial Chemical Industries Limited, London, England

[21] Appl. No.: 69,501

[22] Filed: Aug. 24, 1979

Related U.S. Application Data

[63] Continuation of Ser. No. 781,868, Mar. 28, 1977, abandoned.

[30] Foreign Application Priority Data

Apr. 2, 1976 [GB] United Kingdom ............... 13442/76  
Dec. 8, 1976 [GB] United Kingdom ............... 51198/76

[51] Int. Cl.³ .......................... C12N 1/32; C12N 1/20  
[52] U.S. Cl. .................................. 435/247; 435/253; 435/813  
[58] Field of Search ............... 435/247, 253, 313, 813, 435/315, 3

[56] References Cited

U.S. PATENT DOCUMENTS 3,769,176 10/1973 Hise et al. ............................ 435/315  
3,989,594 11/1976 MacLennan et al. ............... 435/247  
4,048,017 9/1977 Roesler ................................ 435/247

FOREIGN PATENT DOCUMENTS 1417486 12/1975 United Kingdom .  
1417487 12/1975 United Kingdom .

Primary Examiner—Thomas G. Wiseman  
Attorney, Agent, or Firm—Cushman, Darby & Cushman

[57] ABSTRACT

A process of general applicability in the microbiological field wherein a culture is subjected to periods of availability and non-availability of an essential energy source such as a carbon source, i.e. the energy source is supplied in pulses. The efficiency of the culture in converting substrate carbon to cellular carbon varies depending upon the relative duration of the periods of availability and non-availability of the energy source. Thus depending upon the relative duration chosen the process can be applied differently, i.e. when the efficiency is high the process is suitable for single cell protein production while when it is low it is suitable for waste water treatment.

9 Claims, 3 Drawing Figures

PROCESS FOR CULTURING CELLS

This is a continuation, of application Ser. No. 781,868 filed Mar. 28, 1977, now abandoned.

Thus invention relates to a process for culturing cells and in particular to a process for culturing microorganisms, e.g bacteria, yeasts and fungi. The process is however, not restricted to culturing microorganisms and can also be applied to, for example, tissue culture.

The yield in terms of biomass produced to energy supplied in our practical microbiological processes was frequently below the maximum yield which was known to be attainable, and we identified the intermittent nature of energy availability to the cell to be the cause.

In this specification when we refer to an energy source we mean an energy source which is a limiting factor to the rate of growth of the culture concerned. Thus when the energy source is the carbon source we are referring to a culture growing in carbon limitation.

By the intermittent nature of energy availability we mean the variations in the concentration of the energy source in the growing culture which result from deviations from a steady supply of the energy source in the substrate. These concentration changes in the culture will result in variations in the specific growth rate or vice versa. It is the occurence of these periods of substantially zero specific growth rate which affects the overall bioenergetic efficiency of the organisms rather than the apparent effects of variability of energy supply to the whole culture.

We apply the latter by the provision of mechanical devices which can deliver energy source in pulses to the microbial culture.

When an energy source is supplied to a culture in pulses it is supplied in discrete amounts over given periods of time. Each perid of supply is followed by a period during which the energy which has been supplied is available for use by the culture. When all the energy that has been supplied has been used there follows a period during which no energy is supplied to or is available to the culture. In this specification by pulse time we mean the period of time during which energy is supplied to the culture plus the following period during which the energy which has been supplied is available for use by the culture. By cycle time we mean pulse time plus the following time interval during which no exogenous energy is available to the culture, i.e the total period between the commencement of one period of energy supply and the commencement of the next such period said total period necessarily including a period when no exogenous energy is available to the culture.

We have performed experiments in which an energy source such as a carbon source is made available in a growing culture of microorganisms in pulses of both regular and irregular frequency. By pulses of regular frequency we mean pulses comprising equal quantities of the energy source, e.g the carbon source, added in periods of equal time and separated by other equal periods of time. By pulses of irregular frequency we mean periods of energy source made available in any manner other than that defined above as regular, for instance periods whose frequency vary in a random manner and also periods of differing frequency, the differing frequencies following a repeating pattern. From the results of these experiments we have constructed the graph shown in FIG. 1 of the drawings. In the graph the ordinate is the biomass efficiency ratio (varying from 0–1.0) for the culture which is the ratio of the observed energy conversion efficiency of a biological system (as hereinafter defined), obtained in an environment subjected to an intermittent availability of energy, to the energy conversion efficiency of a similar system subjected to continuous availability of energy source. In the graph the abscissa, which is a logarithmic scale, is the cycle time.

The abscissa is also the arithmetic mean cycle time when the cycles are irregular. Where such irregular cycles are not widely distributed about the mean the measured efficiency ratio is substantially in agreement with the graph shown in FIG. 1. Where, however, there is a wide distribution of the cycles about the mean, the measured efficiency ratio does not accord with this graph but is in agreement with a computation of the factor arrived at by a consideration of the weighted mean of the efficiency ratios pertaining to individual cycles. The graph shows the following three regions namely:

A first region in which the cycle time is low, i.e the pulse rate (cycles/unit time) is high, and the energy conversion to biomass efficiency ratio is practically unity and substantially constant. Thus no deleterious effects on energetic efficiency are observed.

A second region in which the cycle time is greater than in the first region, i.e the pulse rate is lower and the energy to biomass efficiency ratio first declines to a minimum and then with increased cycle time reapproaches a constant higher value, ie forming a trough in the graph:

A third region in which the cycle time is greater than in the second region i.e the pulse rate is lower and the efficiency ratio is substantially constant. The efficiency ratio in this region can be the same or lower than its value in the first region. This third region ends when the pulse rate becomes so low that the overall efficiency of the culture falls as microorganisms present in the culture die in appreciable numbers.

The graph described above relates to the case where the time spent by the culture growing at a high rate during a cycle in response to availability of energy source is substantially smaller than the total cycle time. For practical purposes the fraction of time spent growing in this way can, by an approximation, be represented by the ratio of imposed overall specific growth rate ($\mu$) to the maximum specific growth rate ($\mu_{max}$)($\mu_m$) attainable by that culture when unlimited by the availability of carbon and energy source. We have discovered that as the imposed overall specific growth rate approaches $\mu_m$ or as $\mu_m$ is caused to be reduced such that it approaches u, then the influence of the efficiency ratio on the energetic efficiency of the cultures increases at any constant pulse rate. It is appreciated that changes in the specific growth rate of the culture with continuously available but limiting energy source may itself cause changes in the energetic efficiency of a culture. The efficiency ratio previously described relates solely to the additional effects caused by an intermittently available energy source. Conversely decreases in the ratio of u to $\mu_m$ in a culture where the energy source is intermittently available give decreased energetic efficiency at any constant pulse rate when compared with the corresponding culture in which the energy source is continuously available.

These results are shown in a second graph (FIG. 2) having the same co-ordinates as that of FIG. 1 and are represented by a series of lines for different values of $\mu/\mu_m$ which indicate the effect of changing the proportion of time spent in rapid growth in any one cycle.

Figure 3:
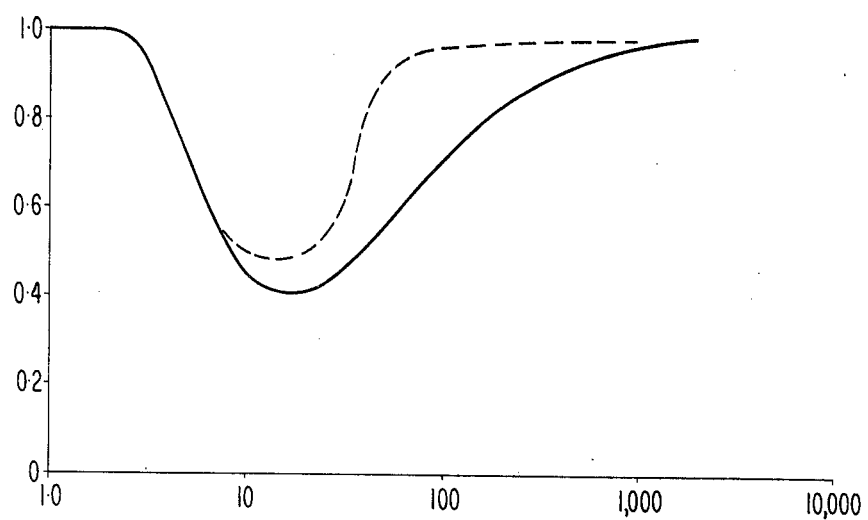

A third graph, FIG. 3, displays the effect that can be obtained when the cycles of energy availability are strictly regular. A significant reduction in the effect caused by the intermittent availability of energy is observed. In this specification the energy conversion efficiency is to be understood to mean the ratio of energy source that is conserved to form biomass divided by the total energy source utilized; for example where the sole energy source is a carbon containing compound it is the ratio of the mass of carbon that is incorporated in the biomas produced divided by the total mass of carbon utilized.

Variations or pulses in the energy supplied to the culture can result in the aforementioned cycles of energy availability and non-availability to the culture where the pulses in supply are sufficient to allow the organism to deplete the energy source reserves in the culture medium. The pulsing of energy supplies to the culture i.e the occurence of time intervals between successive supplies to the culture, may happen in two distinct ways or by any combination of these two distinct ways. In the first way the energy may be supplied to a culture, for example in a tank fermenter, in pulses separated by intervals of time, which time intervals may be controlled. Alternatively in the second way there may be spatial intervals between successive energy supply points to a culture flowing along a pathway defined by physical constraints, the energy source being supplied continuously at the supply points. These two ways may be combined by supplying the energy in pulses separated by intervals of time at the spaced supply points in the second way. In the second way, the effect is to cause individual cells in the culture as they flow along the defined pathway to be exposed to concentration changes which are the equivalent of a pulsed source of energy. In the second way, the distance apart of successive energy supply points and the velocity of flow of the culture between the points determine the equivalent of the cycle time in the first way. This equivalent cycle time will hereinafter also be referred to as the cycle time. The second way may be employed in the fermenters of UK Pat. Nos. 1 353 008; 1 417 486 and 1 417 487.

According to a first embodiment of a first aspect of the invention we provide a process for culturing cells wherein a culture of cells is caused to flow along a pathway defined by physical constraints and an energy source is supplied to the culture at one or more positions thereby causing individual cells in the culture as they flow along the pathway to be exposed to concentration changes which are either effectively negligible or are equivalent to a pulsed source of energy such that the cycle time (as hereinbefore defined) is either effectively zero or falls within said first region of a graph of cycle time against biomass efficiency ratio under the environmental conditions applicable to the culture or falls in the part of the second region of the graph immediately following the first region and is such that the energy efficiency ratio is within 15% of the value in the first region.

According to a second embodiment of the first aspect of the invention we provide a process for culturing cells wherein a culture of cells is caused to flow along a pathway defined by physical constraints and an energy source is supplied to the culture at one or more positions thereby causing individual cells in the culture as they flow along the pathway to be exposed to concentration changes equivalent to a pulsed source of energy which is such that the cycle time (as hereinbefore defined) falls within said first region of a graph of cycle time against biomass efficiency ratio under the environmental conditions applicable to the culture or falls in the part of the second region of the graph immediately following the first region and is such that the energy efficiency ratio is within 15% of the value in the first region.

According to a third embodiment of the first aspect of the invention we provide a process for culturing cells wherein a culture of cells is caused to flow along a pathway defined by physical constraints and an energy source is supplied to the cuture at one or more positions thereby causing individual cells in the culture as they flow along the pathway to be exposed to concentration changes which are either effectively negligible or are equivalent to a pulsed source of energy such that the cycle time (as hereinbefore defined) is either effectively zero or, at a given value of $\mu/\mu_m$, is not greater than that tabulated below; the maximum cycle times for values of $\mu/\mu_m$ falling between any successive pair of the tabulated values being in linear proportion to the cycle times for that pair:

| $\dfrac{\mu}{\mu_m}$ | cycle times (seconds) |
|---|---|
| greater than 0.5 | 30 |
| 0.2 | 6 |
| 0.1 | 4 |
| 0.05 | 3 |
| less than 0.02 | 2.5 |

Preferably in the first aspect the cycle time at a given value of $\mu/\mu_m$ is not greater than that tabulated below, the maximum cycle times for values of $\mu/\mu_m$ falling between any successive pair of the tabulated values being in linear proportion to the cycle times for that pair:

| $\dfrac{\mu}{\mu_m}$ | cycle times (seconds) |
|---|---|
| greater than 0.5 | 15 |
| 0.2 | 5 |
| 0.1 | 3.5 |
| 0.05 | 2.5 |
| less than 0.02 | 2 |

The first aspect of the invention is suitable for processes in which high carbon to cell conversion efficiency is required for instance in processes for the production of single cell protein by culturing microorganisms on a suitable carbon source, e.g methanol. Such a process is described in U.S. Pat. No. 3,989,594. The first aspect is suitably performed in a fermenter such as described in U.S. Pat. No. 3,847,748 or UK Pat. Nos. 1 417 486 or 1 417 487.

In performing processes in which high carbon to cell conversion efficiency is required in apparatus in which a culture flows along a pathway defined by physical constraints, it is preferred to supply the carbon source effectively continuously to the culture to give instant, homogeneous distribution of the carbon source. For practical reasons well known in the art this situation cannot be achieved in certain circumstances, for example where the substrate is a highly soluble fluid and/or where the organism has a high affinity for the energy source. In operating the first aspect of the invention, it is preferred to supply the energy, e.g the carbon source, to the culture at as short a cycle time as possible given the constraints in any particular process. Preferably a plurality of energy source supply points should be provided. The distances apart of successive supply points around the pathway necessary to achieve a suitable cycle time will depend upon the velocity of flow of the culture along the pathway.

Difficulties in supplying an energy source effectively continuously to a culture may sometimes be overcome by using a sparingly soluble substrate such as an alkane, long chain alcohol or a hydrocarbon supplied as a gas or vapour by entrainment in a carrier or by modifying the affinity of the organism for the substrate.

The cycle times quoted above are very suitable for processes for the production of single cell protein from methanol, preferably using strains of the species *Methylophilus methylotrophus* (previously know as *Pseudomonas methylotropha*), the characteristics of which species are described in UK Pat. No. 1 370 892. Very suitable strains of this species are strains NCIB Nos. 10508 to 10515 and 10592 to 10596 (equivalent to NRRL Nos. B 5352-64 and FERM 1215-27). Preferably the velocity of the culture along the pathway is controlled and/or the rate of addition of the energy, e.g the carbon source, at the supply points is controlled.

According to a first embodiment of a second aspect of the invention we provide a process for the biological treatment of liquid carrying biologically degradable material in solution and/or suspension which comprises a step wherein the liquid is supplied continuously and/or in pulses at one or more positions to a treatment vessel containing a culture of microorganisms, thereby exposing individual microorganisms in the culture to a pulsed source of biologically-degradable material or to concentration changes equivalent to such a pulsed source which is such that the cycle time (as hereinbefore defined) falls within the second region of a graph of cycle time against biomass efficiency under the environmental applicable to the culture.

According to a second embodiment of the second aspect of the invention we provide a process for the biological treatment of liquid carrying biologically-degradable material in solution and/or suspension which comprises a step wherein the liquid is supplied continuously and/or in pulses to a treatment vessel containing a culture of microorganisms at one or more positions thereby exposing individual microorganisms in the culture to a pulsed source of biologically-degradable material or to concentration changes equivalent to such a pulsed source which is such that the cycle time (as hereinbefore defined) at a given value of $\mu/\mu_m$ is within the range tabulated below for that value of $\mu/\mu_m$, the ranges for values of $\mu/\mu_m$ falling between any successive pair of the tabulated values being in linear proportion to the cycle times for that pair;

| $\frac{\mu}{\mu_m}$ | cycle times (seconds) |
|---|---|
| greater than 0.2 | 8 to 60 |
| 0.1 | 4.5 to 120 |
| 0.05 | 3.5 to 240 |
| 0.02 | 2.5 to 600 |
| less than 0.01 | 2 to 1200 |

Preferably in the second aspect the cycle time at a given value of $\mu/\mu_m$ is within the range tabulated below for that value of $\mu/\mu_m$, the ranges for values of $\mu/\mu_m$ falling between any successive pair of the tabulated values being in linear proportion to the cycle times for that pair:

| $\frac{\mu}{\mu_m}$ | cycle times (seconds) |
|---|---|
| greater than 0.1 | 8 to 40 |
| 0.05 | 5 to 80 |
| 0.02 | 3.5 to 200 |
| 0.01 | 3 to 400 |
| less than 0.005 | 2.5 to 900 |

The second aspect of the invention is most suitable as a step in any process for the biological treatment of wastewater. It may be used in an aerobic process producing carbon dioxide. In the treatment of wastewater it is desirable that sludge production should be reduced to a minimum and that carbon conversion efficiency of the microorganisms involved in the biological treatment should be low. Hence it is preferred that the energy source, in this instance supplies of wastewater containing biologically degradable material is supplied in the manner described above. Additionally however it will be seen from the graph in FIG. 3 that the use of irregular pulses could be more advantageous than the use of regular pulses in this application.

According to a first embodiment of a third aspect of the invention we provide a process for the fermentation of a culture of cells to produce an organic solvent and/or simple organic molecules wherein an energy source is supplied continuously and/or in pulses to the culture at one or more positions thereby exposing individual cells in the culture to a pulsed source of energy or to concentration changes equivalent to a pulsed source of energy which is such that the cycle time (as hereinbefore defined) falls within the second region of a graph of cycle time against biomass efficiency ratio under the environmental conditions applicable to the culture.

According to a second embodiment of the third aspect of the invention we provide a process to produce an organic solvent and/or simple organic molecules by culturing cells wherein an energy source is supplied continuously and/or in pulses to the culture at one or more positions thereby exposing individual cells in the culture to a pulsed source of energy or to concentration changes equivalent to a pulsed source of energy which is such that the cycle time at a given value of $\mu/\mu_m$ is within the range tabulated below for the value of $\mu/\mu_m$, the ranges for values of $\mu/\mu_m$ falling between any successive pair of the tabulated values being in linear proportion to the cycle times for that pair:

| $\frac{\mu}{\mu_m}$ | cycle times (seconds) |
|---|---|
| greater than 0.2 | 8 to 60 |
| 0.1 | 4.5 to 120 |
| 0.05 | 3.5 to 240 |
| 0.02 | 2.5 to 600 |
| less than 0.01 | 2 to 1200 |

Preferably in the third aspect the cycle time at a given value of $\mu/\mu_m$ is within the range tabulated below for that value of $\mu/\mu_m$, the ranges for values of $\mu/\mu_m$ falling between any successive pair of the tabulated values being in linear proportion to the cycle times for that pair;

| $\frac{\mu}{\mu_m}$ | cycle times (seconds) |
| --- | --- |
| greater than 0.1 | 8 to 40 |
| 0.05 | 5 to 80 |
| 0.02 | 3.5 to 200 |
| 0.01 | 3 to 400 |
| less than 0.005 | 2.5 to 900 |

Examples of solvent fermentations in which the third aspect may be conveniently used include fermentations to produce ethanol, other alcohols, organic acids, ketones, diols and aldehydes. The energy source is usually the carbon source.

The second and third aspects of the invention are similar in that in processes using them it is desired that the efficiency of carbon conversion to cells should be low. Therefore supplies of biologically-degradable material in the second aspect or of energy in the third aspect should be pulsed in such a manner that the processes are operating at or near minimum values of the energy efficiency ratio. Preferably biologically-degradable material or energy is supplied in irregular pulses in order to maximise the desired effect.

Preferably in the second and third aspects the cycle time is such that it falls in a part of the second region of the graph where the efficiency ratio is less than 85% of the values in the first and third regions respectively.

According to a first embodiment of a fourth aspect of the invention we provide a process for culturing cells wherein an energy source is supplied continuously and/or in pulses to the culture at one or more positions thereby causing individual cells in the culture to be exposed to a pulsed source of energy or to concentration changes equivalent to a pulsed source of energy which is such that the cycle time (as hereinbefore defined) falls within said third region of a graph of cycle time against biomass efficiency ratio under the environmental conditions applicable to the culture or falls in the part of the second region of the graph immediately proceding the third region and is such that the efficiency ratio is within 15% of the value in the third region.

According to a second embodiment of the fourth aspect of the invention we provide a process for culturing cells wherein an energy source is supplied continuously and/or in pulses to the culture at one or more positions thereby causing individual cells in the culture to be exposed to a pulsed source of energy or to concentration changes equivalent to a pulsed source of energy which is such that the cycle time (as hereinbefore defined) at a given value of $\mu/\mu_m$ is within a range between the minimum tabulated below and a maximum value at which the overall efficiency of the culture falls and microorganisms present in the culture die in appreciable numbers, the minima for values of $\mu/\mu_m$ falling between any successive pair of the tabulated values being in linear proportion to the cycle times for that pair:

| $\frac{\mu}{\mu_m}$ | cycle times (seconds) |
| --- | --- |
| greater than 0.5 | 40 |
| 0.2 | 120 |
| 0.1 | 230 |
| 0.05 | 450 |
| 0.02 | 1000 |

-continued

| $\frac{\mu}{\mu_m}$ | cycle times (seconds) |
| --- | --- |
| less than 0.01 | 2000 |

Preferably in the fourth aspect the minimum cycle time at a given value of $\mu/\mu_m$ is that tabulated below, the minimum time for values of $\mu/\mu_m$ falling between any successive pair of the tabulated values being in linear proportion to the minimum times for that pair:

| $\frac{\mu}{\mu_m}$ | cycle times (seconds) |
| --- | --- |
| greater than 0.5 | 65 |
| 0.2 | 170 |
| 0.1 | 350 |
| 0.05 | 700 |
| 0.02 | 1800 |
| less than 0.01 | 3600 |

The fourth aspect of the invention may be used in processes for the production of single cell protein, preferably in processes and using fermenters as described above in connection with the first embodiment. However the fourth aspect is more suitably used in processes for the production of extra-cellular or intra-cellular metabolites, for example citric acid, amino acids and antibiotic substances. These processes too are also conveniently performed in the fermenters mentioned above in connection with the first aspect.

Preferably in the fourth aspect of the invention energy, usually the carbon source, is supplied to the culture in regular pulses.

The second, third and fourth aspects may be performed in any suitable apparatus including tank reactors and where appropriate apparatus wherein the culture flows along a pathway defined by physical constraints. It will be understood that when the apparatus is a tank reactor the liquid or energy source is supplied to a culture therein in pulses at one or more positions and that when the culture is flowing along a pathway defined by physical constraints the liquid or energy source is supplied to the culture flowing along the pathway at one or more positions continuously and/or in pulses.

Thus the process of the invention is applicable widely and is very useful in processes involving the continuous culture of microorganisms. It may be used either to increase or decrease the efficiency of cell production in terms of energy used depending upon the type of process in which it is employed. For the production of single cell protein or cell metabolites this efficiency should be maximised. Whilst, as previously mentioned, in wastewater treatment and in the production of organic solvents it should be minimised.

The energy source is suitably the carbon source. However, it may be a light source in a photosynthetic reaction or hydrogen in cultures which can utilize hydrogen as an energy source and other reduced inorganic energy sources in chemolithotropic microorganisms.

Figure 2:
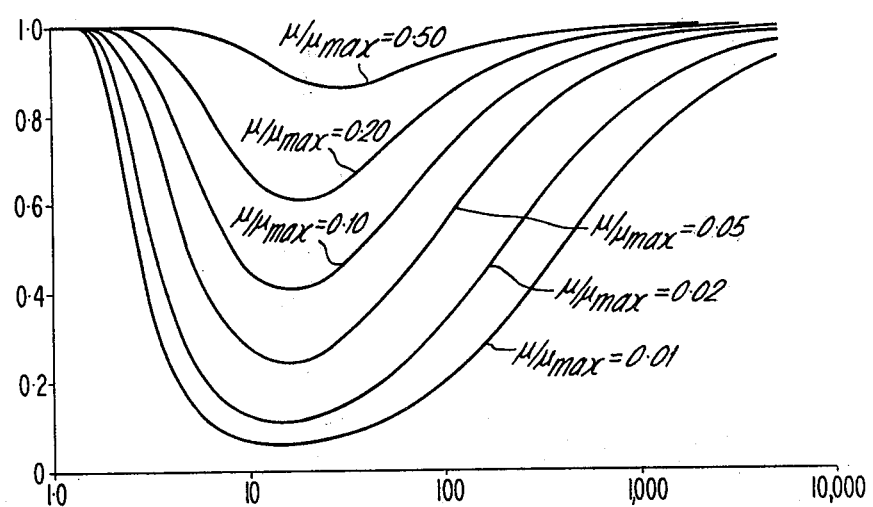

The experiments which we have conducted and from the results of which we have derived the graphs shown in FIGS. 1–3 of the drawings were basically of four types:

1. Experiments in which a culture of microorganisms was circulated around a system comprising a pair of linked identical fermenters. A carbon source was supplied to the culture in various ways namely:
  (a) At an equal rate to each fermenter.
  (b) To one fermenter only.
  (c) To each fermenter but with the rate to one fermenter differing from that to the other.
2. Experiments in which a carbon source was pulsed in a series of different ways into a culture in a standard 2 liter laboratory fermenter.
3. Experiments in which a carbon source was fed continuously at a series of positions into a circulatory fermenter of 50000 liter capacity.
4. Experiments in which wastewater was fed into a circulatory activated sludge system of capacity 2000 liter.

In a continuous culture where growing organisms are supplied with a carbon and/or energy source such that periods of energy starvation occur we believe that when energy is supplied to cells after a period of energy starvation a proportion of the energy supplied is initially used by the cells in a period of adaptation to a growing state and is therefore effectively not available for efficient growth. This represents an overall fall in the efficiency of production of biomass in terms of the energy source consumed over a longer period.

We argue that cells subjected to a truly continuous supply of an energy source such as a carbon source grow in a true steady state where metabolite pools and enzyme activities are at effectively constant levels commensurate with efficient biomass formation. Such cultures can be made inefficient by supplying the energy source in pulses separated by time intervals. The efficiency ratio introduced by this can be broadly defined by an equation of the simplified form:

$$X/(X+fY\mu_m/\mu t)$$

where X is related to the energy required for useful biosynthesis under steady state growth conditions at a rate equal to $\mu_m$, the quantity Y is related to the energy required to reorganise the metabolic apparatus after a protracted period of exogenous energy unavailability, t is the cycle time as hereinbefore defined and f is a factor ranging between 0 and 1.0 describing the proportion of the reorganisational energy required as a function of the time spent without exogenous energy available.

When the term $fY\mu_m/\mu$ is small the efficiency ratio approximates to unity. This can be achieved by: increasing $\mu$ at constant $\mu_m$; decreasing $\mu_m$ at constant $\mu$ or by the value of function f changing with cycle time. The function f is a complex function describing the fraction of metabolite pools degraded during a period without exogenous energy available and as such contains; rate constants (k) for pool metabolism; a response time ($t_r$) between energy depletion and the onset of metabolite degradation; the total cycle time (t) and the proportional growth factor $\mu/\mu_m$;

Assuming that after depletion of the energy supply the organism remains unaffected for a response time ($t_r$) and thereafter the metabolite pools are used up at a rate proportional to their residual concentration then it can be shown that:

$$f = 1 - \exp(kt_r - kt(1 - \mu/\mu_m))$$

(provided that f=0 is substituted when values less than zero are derived) This is at best an approximation but it gives a good representation except at the end of the response time where an instantaneous change from a zero to a finite rate of metabolite usage is predicted. This is not in accord with our understanding of real microbiological systems so some smoothing of the function in this region has been imposed.

When the value of f is inserted into the equation:

$$\text{Efficiency Ratio} = X/(X+fY\mu_m/\mu t)$$

the resultant equation describes a series of lines as shown in FIG. 2. All our data fit on these lines.

In FIG. 1 the first region of the graph previously described is interpreted in the following manner. At these very short cycle times the influence of the delayed response time of the organisms is such that f tends to zero and the efficiency ratio is at a maximum. In the second region of the graph f has increased because the cycle time now substantially exceeds the response time of the organism and thus the efficiency ratio decreases. However, as t continues to be increased then the influence of f on the equation declines and t becomes the dominant influence with the result that the efficiency ratio increases. In this region the typical graph for regular pulses diverges from that for irregular pulses as in FIG. 3. For regular pulses the reapproach to a constant value is displaced towards shorter cycle times. The reason for this last observation is probably that natural oscillations of regular frequency that cells use for regulating metabolic activities efficiently may be tuned or entrained by the correct constant frequency of substrate pulsing (i.e. regular pulses). When irregular pulses are used the natural constant frequency of metabolic oscillations is destroyed and random inefficient variations in activity occur. Experience with pure cultures growing on a single energy source (protein organism) on methanol and mixed cultures (prokaryotes and eukaryotes) growing on a mixed energy source (domestic effluent) shows that the theory and practice fit the mathematical model that we have derived. We believe that the theory is applicable to most microorganisms growing in energy limited continuous cultures and we have termed it the Reorganisation Energy Loss Theory.

EXAMPLE 1

A culture of *Methylophilus methylotrophus* was grown in a small pressure cycle fermenter (such as that described in U.S. Pat. No. 3,847,748) of 165 l working liquid volume at 40° C. and $D=0.25h^{-1}$. The medium was that described as Medium I in U.S. Pat. No. 3,989,594. The circulation rate within the fermenter was $30m^3h^{-1}$ giving a mean circulation time of 20 seconds. Cell dry weight was related to methanol addition rate such that 14 g/l was the steady state concentration of dry cells. Five methanol addition points were distributed around the fermenter such that, while methanol flows through each point were different, the flows of methanol were proportional to the volume of liquid contained in that portion of the fermenter.

The physical distribution of the methanol addition ports was such that circulating cells were subjected to a consecutive cycle of substrate presence and absence every 3 seconds or to a similar cycle every 20 seconds when all the methanol supplied to the fermenter was added at one point. Results are shown in Table 1.

TABLE 1

| Methanol addition cycle time | C to cells[1] | C to $CO_2$[2] | C S/N[3] |
|---|---|---|---|
| 20 seconds | 57.8 | 38.6 | 4.3 |

TABLE 1-continued

| Methanol addition cycle time | C to cells[1] | C to $CO_2$[2] | C S/N[3] |
|---|---|---|---|
| 3 seconds | 65.1 | 30.9 | 3.2 |

[1] C to cells represents percentage of methanol carbon converted to cellular carbon.
[2] C to $CO_2$ represents percentage of methanol carbon converted to $CO_2$ carbon.
[3] C to S/N represents percentage of methanol carbon converted to supernatant carbon.

EXAMPLE 2

A continuous laboratory fermenter (liquid volume of 1.5 l and steady state dry weight of 10 g/l) culture of *Methylophilus methylotrophus* was grown at various dilution rates with constant medium flows. A separate addition system for methanol was used such that sufficient methanol required for example, 3 seconds of growth at $\mu=0.2h^{-1}$, could be supplied as a pulse of methanol supplied in 0.3 seconds. This ratio of supply time to total cycle time was maintained at 1 to 10 throughout the variations in cycle time. Medium composition and conditions of growth were identical to those described in Example 1. Results are shown in Table 2.

TABLE 2

| Dilution rate ($h^{-1}$) | Cycle time (seconds) | *C cells (%) |
|---|---|---|
| 0.07 | 2.75 | 56.2 |
|  | 5.5 | 49.3 |
|  | 11.0 | 47.5 |
|  | 22.0 | 42.3 |
| 0.20 | 1.0 | 64.4 |
|  | 2.0 | 62.4 |
|  | 2.5 | 61.0 |
|  | 3.0 | 59.5 |
|  | 4.0 | 54.5 |
|  | 8.0 | 53.0 |
|  | 11.0 | 47.1 |
|  | 20.0 | 46.2 |
|  | 33.0 | 48.8 |
| 0.4 | 2.75 | 62.1 |
|  | 5.5 | 61.5 |

*% (w/w) of methanol carbon incorporated into cellular carbon. Carbon content of cells remained constant throughout the experiment.

What is claimed is:

1. A process of culturing cells which comprises the steps of: causing a culture of cells to flow along a pathway defined by physical constraints under cultivation conditions; and supplying an energy source to the culture at one or more fixed positions in amounts controlled so that as individual cells in the culture flow along the pathway at a controlled rate such that they are exposed to effectively negligable energy source concentration changes, wherein the distance between the one or more fixed positions and the flow rates are selected to allow the cells to deplete the energy source reserves before encountering additional energy source.

2. A process for culturing cells comprising the steps of
   (a) causing a culture of cells to flow along a pathway defined by physical constraints under cultivation conditions, and having one or more fixed positions for supplying energy source therealong;
   (b) controlling the flow rate and selecting the relative position and spacing of the fixed positions along the flow path so that the individual cells in the culture flow are exposed to energy source concentration changes;
   (c) supplying an energy source to the culture at one or more fixed energy supply positions along the pathway in discrete amounts over a cycle time t wherein t is a period of time during which energy is supplied to the culture plus a following period during which the energy which has been supplied is available for use by the culture plus a following time interval during which no exogenous energy is available to the culture each period of time or time interval being greater than zero; and
   (d) controlling the cycle time t, so that a function f tends to zero, wherein f is a complex function describing the fraction of metabolite pools degraded during a period without exogenous energy available, and can be approximated, provided that $f=0$ is substituted when values less than zero are derived, by the equation $f=1-\exp(kt_r-kt(1-\mu/\mu_m))$, where k is a rate constant for pool metabolism, $t_r$ is a response time between energy depletion and the one set of metabolite degradation, and $\mu/\mu_m$ is a proportional growth factor; $\mu$ being the imposed overall specific growth rate and $\mu_m$ being the maximum specific growth rate attainable by the particular culture.

3. A process for culturing cells comprising the steps of
   (a) causing a culture of cells to flow along a pathway defined by physical constraints under cultivation conditions, and having one or more fixed positions for supplying energy source therealong;
   (b) controlling the flow rate and selecting the relative position and spacing of the fixed positions along the flow path so that the individual cells in the culture flow are exposed to energy source concentration changes;
   (c) supplying an energy source to the culture at one or more positions along the pathway in discrete amounts over a cycle time t, wherein t is a period of time during which energy is supplied to the culture plus a following period during which the energy which has been supplied is available for use by the culture plus a following time interval during which no exogenous energy is available to the culture each period of time or time interval being greater than zero; and
   (d) controlling the cycle time, t, so that, at a given value of $\mu/\mu_m$, it is not greater than that tabulated below with the maximum cycle times t for values of $\mu/\mu_m$ falling between any successive pair of the tabulated values being in linear proportion to the cycle times t for that pair, where in $\mu/\mu_m$ is a proportion growth factor, $\mu$ being the imposed overall specific growth rate and $\mu_m$ being the maximum specific growth rate attainable by the particular culture:

|  | $\mu/\mu_m$ | t (seconds) |
|---|---|---|
| greater than | 0.5 | 30 |
|  | 0.2 | 6 |
|  | 0.1 | 4 |
|  | 0.05 | 3 |
| less than | 0.02 | 2.5 |

4. A process according to claim 3 wherein the cycle time at a given value of $\mu/\mu_m$ is not greater than that tabulated below, the maximum cycle times for values of $\mu/\mu_m$ falling between any successive pair of the tabulated values being in linear proportion to the cycle times for that pair:

| $\dfrac{\mu}{\mu_m}$ | cycle times (seconds) |
|---|---|
| greater than 0.5 | 15 |
| 0.2 | 5 |
| 0.1 | 3.5 |
| 0.05 | 2.5 |
| less than 0.02 | 2 |

5. A process according to claim 4 for the production of single cell protein by culturing microroganisms on a suitable carbon source.

6. A process according to claim 5 wherein the carbon source is methanol.

7. A process according to claim 6 wherein the energy source is supplied to the culture at a plurality of points around the pathway.

8. A process according to claim 6 wherein the cells belong to the species *Methylophilus methylotrophus* (previously known as *Pseudomonas methylotropha*).

9. A process according to claim 8 wherein the cells belong to any of the strains NCIB Nos. 10508 to 10515 and 10592 to 10596.

* * * * *